(12) United States Patent
Schenden et al.

(10) Patent No.: US 10,973,500 B2
(45) Date of Patent: Apr. 13, 2021

(54) DEVICE AND METHOD FOR ASPIRATING BONE MARROW

(71) Applicant: FOREVER LABS, INC., Ann Arbor, MI (US)

(72) Inventors: Michael Schenden, Bloomfield Hills, MI (US); Mark Katakowski, Ann Arbor, MI (US); Benjamin Buller, Bloomfield Hills, MI (US)

(73) Assignee: FOREVER LABS, INC., Ann Arbor, MI (US)

( * ) Notice: Subject to any disclaimer, the term of this patent is extended or adjusted under 35 U.S.C. 154(b) by 223 days.

(21) Appl. No.: 15/996,015

(22) Filed: Jun. 1, 2018

(65) Prior Publication Data

US 2018/0344298 A1 Dec. 6, 2018

Related U.S. Application Data

(60) Provisional application No. 62/514,579, filed on Jun. 2, 2017.

(51) Int. Cl.
*A61B 10/02* (2006.01)
*A61M 1/00* (2006.01)
*A61B 17/34* (2006.01)
*A61M 5/19* (2006.01)

(52) U.S. Cl.
CPC ........ *A61B 10/025* (2013.01); *A61B 10/0283* (2013.01); *A61M 1/007* (2014.02); *A61B 17/3472* (2013.01); *A61B 2010/0208* (2013.01); *A61B 2010/0258* (2013.01); *A61M 1/008* (2013.01); *A61M 1/0058* (2013.01); *A61M 5/19* (2013.01); *A61M 2202/10* (2013.01)

(58) Field of Classification Search
CPC ...... A61M 1/007; A61M 1/0058; A61M 5/19; A61M 2202/10; A61M 1/008; A61M 2210/02; A61M 2005/3201; A61B 10/0283; A61B 2010/0208; A61B 17/3472; A61B 2010/0258; A61B 10/025
See application file for complete search history.

(56) References Cited

U.S. PATENT DOCUMENTS

| 2012/0035501 | A1* | 2/2012 | Landrigan | A61B 10/025 |
| | | | | 600/567 |
| 2014/0130936 | A1* | 5/2014 | Shippert | A61M 1/007 |
| | | | | 141/2 |
| 2015/0305725 | A1* | 10/2015 | Speiser | A61B 10/0291 |
| | | | | 600/431 |

* cited by examiner

*Primary Examiner* — Theodore J Stigell
*Assistant Examiner* — Daniel Moore
(74) *Attorney, Agent, or Firm* — Marshall, Gerstein & Borun LLP (57) ABSTRACT

A device and method for aspirating bone barrow. The device includes a double syringe assembly having a distal syringe and a proximal syringe coupled to the distal syringe. A plunger includes a distal end disposed within a barrel of the distal syringe and a proximal end disposed within a barrel of the proximal syringe. A needle assembly is coupled to the double syringe assembly and includes a needle having an outer tube and an inner tube disposed within the outer tube. Upon actuation of the plunger, the distal syringe aspirates bone marrow through the outer tube of the needle and into a chamber of the distal syringe. At the same time, the proximal syringe injects fluid through the inner tube of the needle at the same rate in which the bone marrow is aspirated.

18 Claims, 4 Drawing Sheets

DEVICE AND METHOD FOR ASPIRATING BONE MARROW

CROSS-REFERENCE TO RELATED APPLICATIONS

This application claims priority to U.S. Provisional Patent Application No. 62/514,579 filed Jun. 2, 2017, entitled "Device and Method for Aspirating Bone Marrow" the entire disclosure of which is hereby incorporated by reference.

TECHNICAL FIELD

This disclosure relates to aspiration methods and devices and, in particular, to an improved device and method for aspirating bone marrow.

BACKGROUND

Extraction of bone marrow has many medical uses, and employment of treatments that make use of bone marrow concentrate are increasingly being used in physician office settings under local anesthetic. Typically, such extraction procedures produce some discomfort and anxiety in patients, which may lead to limited use even in cases when it would be advantageous to the patient. For example, more recently it has become increasingly common for physicians to perform aspirations of bone marrow in office settings, where patients are awake and under only local anesthetic. A high amount of anxiety can accompany this procedure, which results from the patient anticipating pain. The expectation of pain can lead to patients opting not to elect care that could prevent the necessity for more severe interventions in the future, such as surgical repair of joints.

More specifically, the majority of pain and discomfort is experienced while the marrow is being aspirated. When aspiration occurs, negative pressure is created in a lumen of the bone. The negative pressure acts against the force of the aspiration device. As a result, many patients experience peak discomfort during this period. For example, patients often report a sensation of cramping, which in the case of aspiration from the posterior superior iliac spine (a very common point of entry to the marrow space) can happen anywhere and everywhere from the gluteus muscle, down the leg, and into the feet.

In addition to causing patient discomfort, negative pressure during aspiration slows the rate at which the physician can withdraw the bone marrow. Furthermore, application of excessive aspiration force when aspirating can cause damage, such as hemolysis, to the bone marrow sample via sheer stress or other forces.

SUMMARY OF THE DISCLOSURE

A device for aspirating bone marrow includes a double syringe assembly including a distal syringe with a barrel having a chamber and a proximal syringe coupled to the distal syringe, the proximal syringe having a barrel with a chamber. A single plunger has a distal end disposed within the barrel of the distal syringe and a proximal end disposed within the barrel of the proximal syringe. A needle assembly is coupled to the double syringe assembly. The needle assembly includes a needle with an outer tube and an inner tube disposed within the outer tube, a housing surrounding a portion of the needle, and a connector extending from the housing. The connector is attached to the distal syringe. Upon actuation of the plunger in a direction toward the proximal syringe, the distal syringe extracts bone marrow from a target area through the outer tube of the needle and into the chamber of the distal syringe and the proximal syringe injects fluid into the target area through the inner tube of the needle at the same time and the same rate in which the bone marrow is extracted, the plunger controlling the flow volume of each syringe chamber such that the fluid volume ejected by the chamber of the proximal syringe is equal to the bone marrow volume received by the chamber of the distal syringe.

In yet another example, a double syringe assembly for aspirating bone marrow includes a distal syringe having a barrel with a chamber and a proximal syringe coupled to the distal syringe, the proximal syringe having a barrel with a chamber. A plunger has a distal end disposed within the barrel of the distal syringe and a proximal end disposed within the barrel of the proximal syringe. Upon actuation of the plunger in a direction toward the proximal syringe, the distal syringe receives bone marrow in the chamber of the distal syringe and the proximal syringe ejects fluid disposed within the chamber of the proximal syringe one of before or simultaneous to the bone marrow being received in the chamber of the distal syringe. The plunger controls the flow volume of each chamber such that the fluid volume ejected by the chamber of the proximal syringe is equal to the bone marrow volume received by the chamber of the distal syringe.

In another example, a method of aspirating bone marrow comprises extracting bone marrow from a target area through one of a first needle or an outer tube of a needle of a needle assembly and into a chamber of a distal syringe. The method further comprise injecting fluid from a chamber of a proximal syringe through one of a second needle separate from the first needle or an inner tube of the needle of the needle assembly and into the target area one of before or simultaneous to extracting the bone marrow, preventing negative pressure during aspiration.

In yet another example, a method of aspirating bone marrow comprises extracting tissue from an aspiration hole in a target area and injecting fluid through one or more of the aspiration hole or a separate injection hole in the target area one or more of simultaneous to or before extracting the tissue.

Additional optional aspects and features are disclosed, which may be arranged in any functionally appropriate manner, either alone or in any functionally viable combination, consistent with the teachings of the disclosure. Other aspects and advantages will become apparent upon consideration of the following detail description.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION

Generally, a device and methods for aspirating bone marrow are disclosed. The device and methods mitigate patient pain caused by negative pressure of conventional aspiration devices and methods. For example, the device and methods of the present disclosure significantly reduce or eliminate negative pressure by replacing fluid in the bone marrow target area being aspirated before or during aspiration of the bone marrow. More specifically, and in one example, the device comprises a double syringe assembly including a distal syringe with a barrel having a chamber and a proximal syringe coupled to the distal syringe. The proximal syringe includes a barrel with a chamber, and a single plunger has a distal end disposed within the barrel of the distal syringe and a proximal end disposed within the barrel of the proximal syringe. The distal syringe is for aspirating bone marrow and the proximal syringe for inserting fluid. A needle assembly is coupled to the double syringe assembly and includes a needle with an outer tube and an inner tube disposed within and separate from the outer tube. Upon actuation of the plunger in a direction toward the proximal syringe, the distal syringe aspirates bone marrow from a target area, such as a bone, through the outer tube of the needle and into the chamber of the distal syringe. Simultaneously, the proximal syringe injects fluid, such as one or more of saline or other salt balanced fluid, antibiotics or anesthetic, into the target area through the inner tube of the needle at the same rate in which the bone marrow is aspirated, eliminating negative pressure during aspiration. As a result, the ease of bone marrow withdrawal is improved, the rate of withdrawal may be increased, and the risk of damaging the bone marrow sample may be reduced. Further, patient pain caused by negative pressure is significantly mitigated, if not eliminated, reducing patient anxiety.

In other examples, which are explained more below, the method includes injecting fluid into the target area before aspiration of the bone marrow. In yet another example, the method includes injecting fluid into an injection bore or hole in the target area that is different from an aspiration bore or hole in the target area. In another example, the method includes injecting fluid into the aspiration bore or hole in the target area, which is also used to aspirate the bone marrow from the target area.

Figure 1:
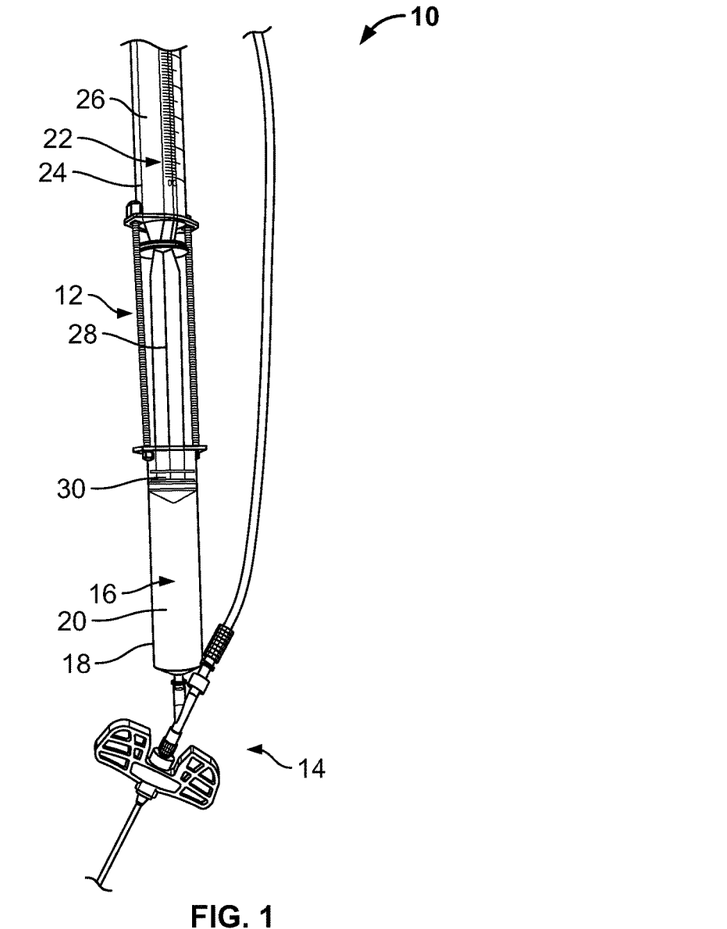
FIG. 1 is a top perspective view of a device for aspirating bone marrow according to one aspect of the present disclosure.

Referring now to FIG. 1, a device 10 for aspirating bone marrow according to one aspect of the present disclosure is depicted. The device 10 comprises a double syringe assembly 12 and a needle assembly 14 coupled to the double syringe assembly 12. The double syringe assembly 12 includes a distal syringe 16 with a barrel 18 having a chamber 20. A proximal syringe 22 is coupled to the distal syringe 16 and also includes a barrel 24 having a chamber 26. A single plunger 28 has a distal end 30 disposed within the barrel 18 of the distal syringe 16 and a proximal end 32 (FIG. 2) disposed within the barrel 24 of the proximal syringe 22, as depicted in FIG. 2.

Figure 2:
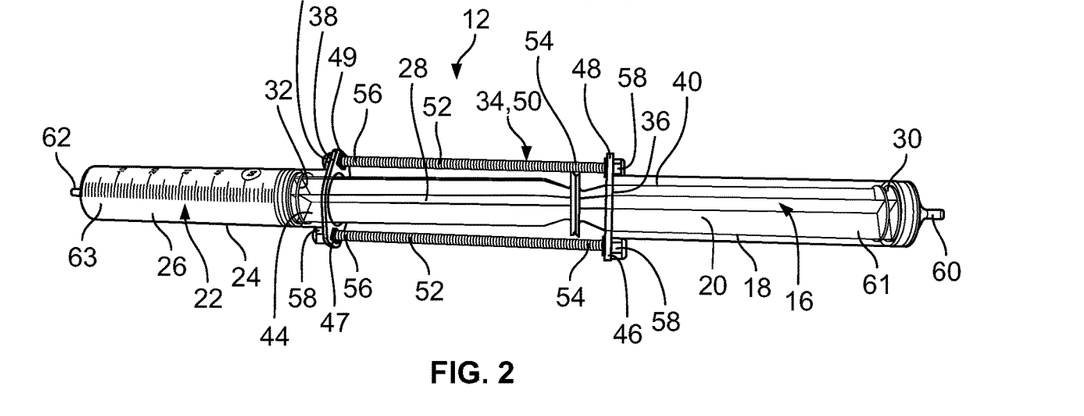
FIG. 2 is a side perspective view of a double syringe assembly according to another aspect of the present disclosure.

Referring now to FIG. 2, another view of the double syringe assembly 12 is depicted. In one example, the double syringe assembly 12 further includes a securing mechanism 34 for coupling the distal syringe 16 to the proximal syringe 22, such that the distal syringe 16 is stationary relative to the proximal syringe 22. In a further example, each of the distal syringe 16 and the proximal syringe 22 include a base portion 36, 38, respectively, attached to each of the barrel 18 of the distal syringe 16 and the barrel 24 of the proximal syringe 22, respectively. For example, the base portion 36 is attached to a proximal end 40 of the distal syringe 16, and the base portion 38 is attached to a distal end 44 of the proximal syringe 22. In addition, each base portion 36, 38 includes at least one aperture 46, 47 or a plurality of apertures 48, 49 for receiving the securing mechanism 34, as described more below.

In one example, the securing mechanism 34 comprises a plurality of rods 50. Each rod 52 includes a first end 54 disposed within the at least one aperture 46 or an aperture from the plurality of apertures 48 of the base portion 36 of the distal syringe 16. Each rod 52 further includes a second end 56 disposed within the at least one aperture 47 or an aperture from the plurality of apertures 49 of the base portion 38 of the proximal syringe 22. In addition, each of the first and second ends 54, 56 of each rod 52 extends through the at least one aperture 46, 47 of the base portions 36, 38 of the distal and proximal syringes 16, 22, respectively. In this manner, the first and second ends 54, 56 are adapted to receive or receive a fastener 58 to secure the first and second ends 54, 56 of the rods 52 to the base portions 36, 38 of the distal and proximal syringes 16, 22, respectively. As one of ordinary skill in the art will appreciate, the fastener 58 may include one or more of a bolt, a screw, or a threaded part capable of securing the rod 52 to the base portions 36, 38 of the distal and proximal syringes 16, 22.

While the aforementioned describes the securing mechanism 34 as the plurality of rods 50 or the at least one rod 52, one of ordinary skill in the art will appreciate that various other securing mechanisms 34 may additionally and/or alternatively be used and still fall within the scope of the present disclosure. For example, and optionally, the securing mechanism 34 may include a plate, such as a cylindrical plate, disposed between the distal syringe 16 and the proximal syringe 22. Alternatively, any other securing mechanism capable of securing the distal and proximal syringes 16, 22 together may be used. In addition, while two rods 52 are depicted in FIG. 2, for example, one of ordinary skill in the art will further appreciate that three, four, five, six, or any additional number of rods capable of being disposed within the base portions 36, 38 may alternatively be used and still fall within the scope of the present disclosure. In the example depicted in FIG. 2, the two rods 52 are equidistantly disposed from each other on the bases of the distal and proximal syringes 16, 22.

Still referring to FIG. 2, the distal syringe 16 may further include a nozzle 60 disposed on a distal end 61 of the distal syringe 16. The nozzle 60 may be coupled to a portion of the needle assembly 14 (FIG. 1), as explained more below relative to FIGS. 3 and 4. In a similar manner, the proximal syringe 22 may further include a nozzle 62 disposed on a proximal end 63 of the proximal syringe 22. The nozzle 62 may also be coupled to the needle assembly 14, as further explained below.

In FIG. 2, the plunger 28 is depicted in an unactuated state, in which the distal end 30 of the plunger 28 is adjacent to the nozzle 60 of the distal syringe 16, and the proximal end 32 of the plunger 28 is adjacent the base portion 38 of the proximal syringe 22. The plunger 28 is moveable from and between the unactuated state and an extended state. In the extended state, which is partially depicted in FIG. 1, the proximal end 32 of the plunger 28 is adjacent to the nozzle 62 of the proximal syringe 22 and the distal end 30 of the plunger 28 is adjacent to the base portion 36 of the distal syringe 16 (not shown).

Figures 3A, 3B:
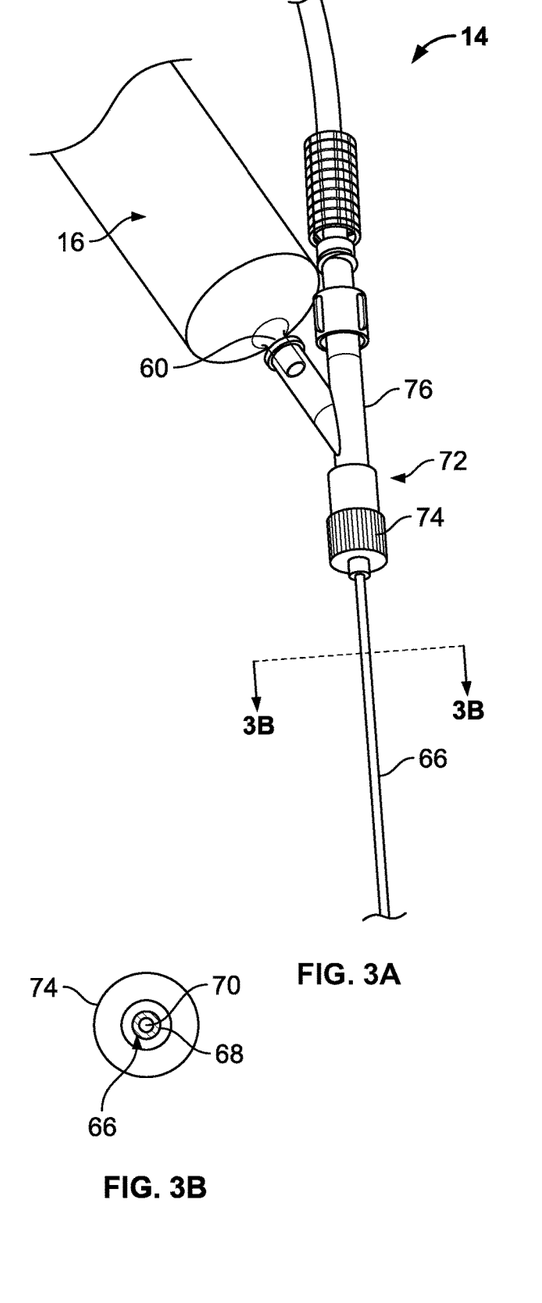
FIG. 3A is perspective view of a portion of the device of FIG. 1.
FIG. 3B is a cross-section view of a needle of the device of FIG. 3A, taken along the lines A-A of FIG. 3A.
Figure 4:
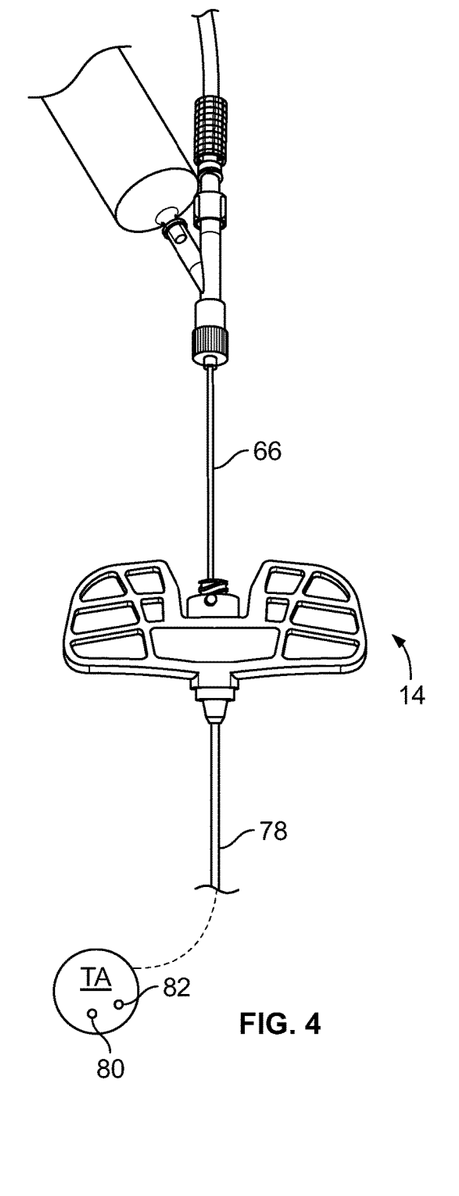
FIG. 4 is another perspective view of another portion of the device of FIG. 1.

Referring now to FIGS. 3A, 3B and 4, portions of the needle assembly 14 of FIG. 1 are further depicted. As depicted in FIGS. 3A and 3B, the needle assembly 14 includes a needle 66. The needle 66 includes an outer tube 68 and an inner tube 70 disposed within and concentric to the outer tube 68, as depicted in FIG. 3B. The needle assembly 14 further includes a housing or housing portion 72 surrounding a portion of the needle 66 and having a body 74 and a connector 76 extending from the body 74, for example. The connector 76 may be a Y-shaped connector, as depicted in FIG. 3A, or any other type of connector known by persons having ordinary skill in the art and still fall within the scope of the present disclosure. In this example, the connector 76 is one or more of attached to or coupled to the nozzle 60 of the distal syringe 16. The connector 76 couples the outer tube 68 of the needle 66 to the nozzle 60 of the distal syringe 16 to form a flow pathway between the outer tube 68 of the needle 66 and the chamber 20 of the distal syringe 16.

In a similar manner, the nozzle 62 of the proximal syringe 22 may be coupled to another connector or tube, as explained more below relative to FIG. 5A. This connector may be attached to the inner tube 70 of the needle 66 to form a second flow pathway, such as a fluid flow pathway. The second flow pathway extends between the inner tube 70 of the needle 66 and the chamber 26 of the proximal syringe 22. As one of ordinary skill in the art will appreciate, the inner tube 70 of the needle 66 is separate and sealed from the outer tube 68 of the needle 66. So constructed, any tissue, such as bone marrow, being extracted through the outer tube 68 is prevented from mixing or interfering with any fluid being injected or inserted from the proximal syringe 22 into the inner tube 70, for example, as one of ordinary skill in the art understands.

So configured, upon actuation of the plunger 28 in a direction toward the proximal syringe 22, the distal syringe 16 aspirates, such as extracts, bone marrow from a target area TA (FIG. 4) through the outer tube 68 of the needle 66 and into the chamber 20 of the distal syringe 16. Simultaneously, the proximal syringe 22 injects fluid into the target area TA through the inner tube 70 of the needle 66 at the same rate in which the bone marrow is aspirated. In this way, the plunger 28 controls the flow volume of each chamber 20, 26 of the distal syringe 16 and the proximal syringe 22, respectively. As a result, the fluid volume ejected from the chamber 26 of the proximal syringe 22 is equal to the bone marrow volume received in the chamber 20 of the distal syringe 16.

Referring now to FIG. 4, the target area TA through which bone marrow is extracted is depicted. The target area TA is coupled to the needle assembly 14, for example, during aspiration. Said another way, a cannula 78 of the needle assembly 14 is coupled to the needle 66 and inserted into an aspiration bore 80 of the target area TA to begin aspiration or extraction, for example. In other example methods, as explained more below, a needle separate from the needle 66 may alternatively be used to inject the fluid into the target area TA before or simultaneous to the extraction of the bone marrow from the target area TA. In this example, a needle separate from the needle 66 may be inserted into the aspiration hole 80 before the needle 66 is inserted for extraction or inserted into an injection hole 82, separate from the aspiration hole 80, as depicted in FIG. 4. In one example, the target area TA is a lumen of a bone, such as a bone disposed in a posterior superior iliac spine area, which is a common point of entry for a marrow space in the lumen of the bone. As one of ordinary skill in the art will appreciate, the target area TA may alternatively include any other area of a subject, such as the human body, in which bone marrow is desired to be extracted, for example.

The fluid disposed within the chamber 26 of the proximal syringe 22 may be one or more of saline, a salt-balanced sterile solution, an antibiotic or an anesthetic. One of ordinary skill in the art will appreciate that any other fluid providing a positive pressure, for example, into the target area to one or more of reduce, neutralize, or zero-out the negative pressure produced during extracting of the bone marrow, may alternatively be used and still fall within the scope of the present disclosure.

Figure 5A:
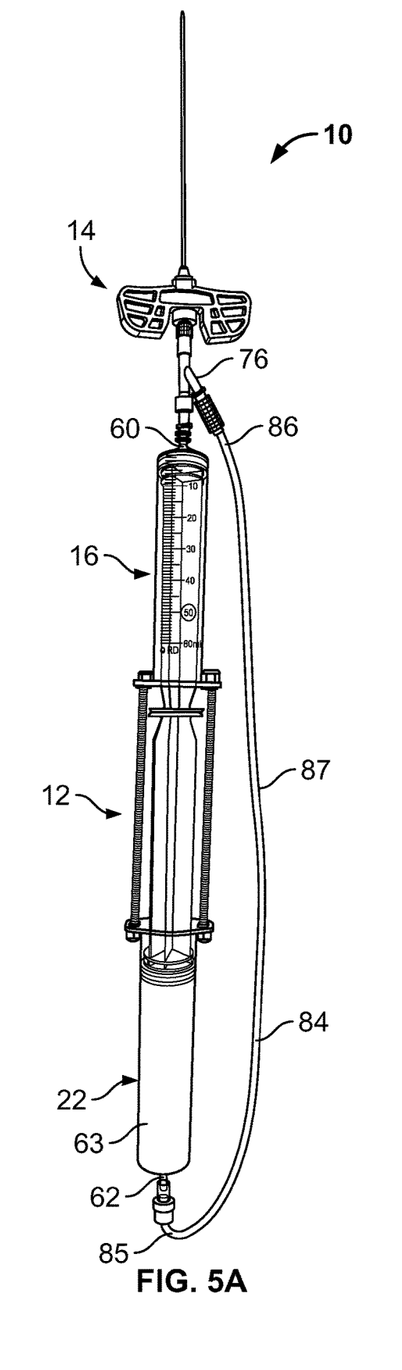
FIG. 5A is another perspective view of the device for aspirating bone marrow according to one aspect of the present disclosure.

Referring now to FIG. 5A, another perspective view of the device 10 for aspirating bone marrow is depicted. In this view, the nozzle 60 of the distal syringe 16 is coupled to the needle assembly 14 and the nozzle 62 of the proximal syringe 22 is coupled to an injection tube 84 that receives fluid ejected from the proximal syringe 22 during operation of the device 10. The fluid flows through the injection tube 84 and into the needle assembly 14, as depicted. More specifically, the injection tube 84 includes first end 85 that is coupled to the nozzle 62 of the proximal syringe 22 and a second end 86 that is coupled to the connector 76 of the needle assembly 14.

So configured, a second flow pathway 87, such as a fluid flow pathway, is formed between the nozzle 62 of the proximal syringe 22 and the needle assembly 14 coupled to the distal syringe 16. In this way, the injection tube 84 is coupled to the inner tube 70 of the needle 66 of the needle assembly 14, allowing injection of the fluid from the injection tube 84 and into the needle 66 during operation. As noted, the inner tube 70 of the needle 66 is separate and sealed from the outer tube 68 of the needle 66. So constructed, any tissue being extracted through the outer tube 68 of the needle 66 is prevented from mixing or interfering with any fluid being injected or inserted from the proximal syringe 22, through the injection tube 84, and into the inner tube 70 of the needle, for example.

Figure 5B:
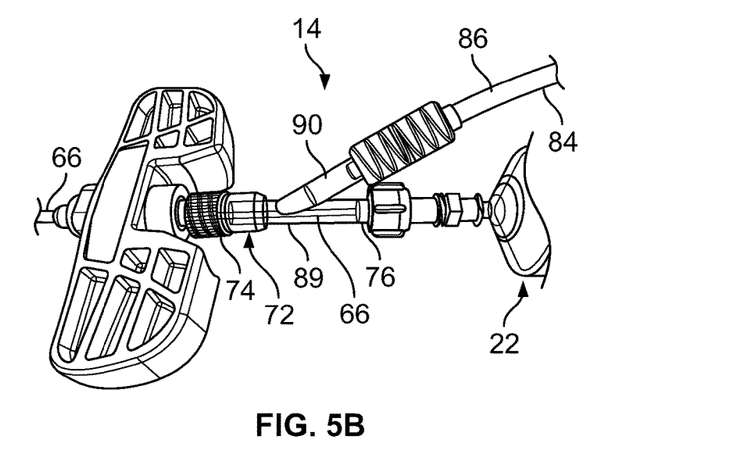
FIG. 5B is a perspective view of a portion of the device of FIG. 5A.

As further depicted in FIG. 5B, the second end 86 of the injection tube 84 is coupled to a portion of the connector 76. More specifically, the connector 76 includes a first leg 89 having a longitudinal axis parallel to a longitudinal axis of the housing 72 of the needle assembly 14. The connector 76 further includes a second leg 90 that extends from the first leg 89 at an angle from the longitudinal axis of the first leg

89, such that the second leg 90 of the connector 76 is not parallel to the longitudinal axis of the first leg 89 and the housing 72. The second end 86 of the injection tube 84 is coupled to the second leg 90 of the connector 76, allowing the injection tube 84 to be coupled to the inner tube 70 of the needle 66.

Figure 5C:
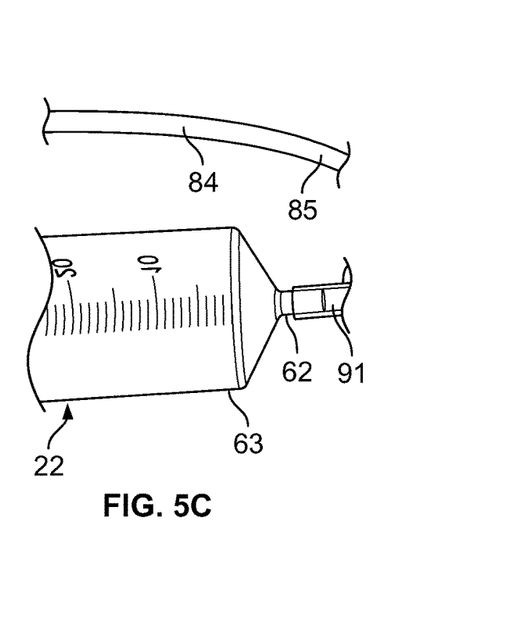
FIG. 5C is a perspective view of another portion of the device of FIG. 5A

Referring now to FIG. 5C, another portion of the device 10 of FIG. 5A is depicted. More specifically, a close-up view of the nozzle 62 of the proximal syringe 22 is depicted. In one example, the first end 85 of the injection tube 84 further includes a connecting portion 91 that fits around the nozzle 62 to couple the injection tube 84 to the proximal syringe 22. In this way, fluid disposed within the proximal syringe 22 may be ejected through the nozzle 62 and into the injection tube 84 for insertion into the inner tube 70 of the needle 66.

Figure 6:
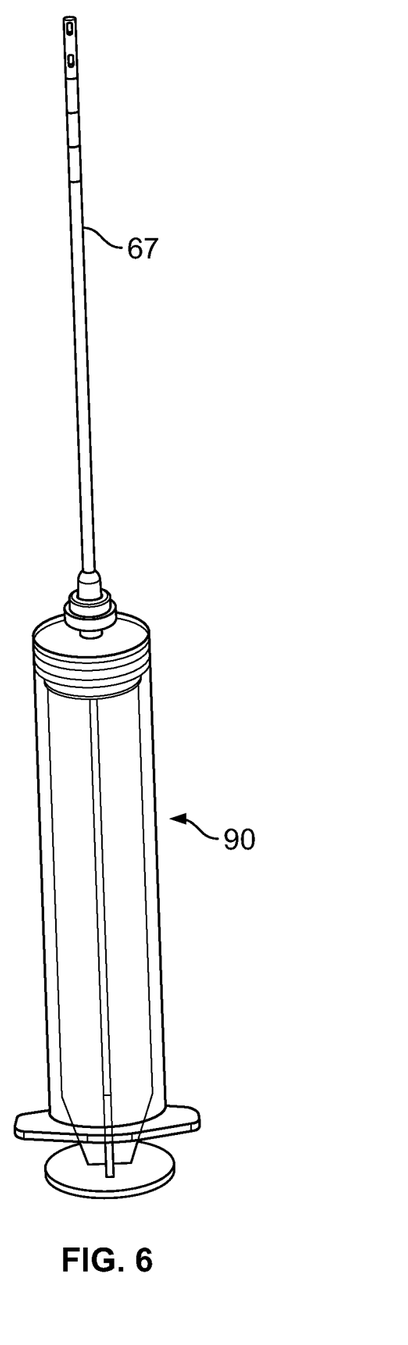
FIG. 6 is a perspective view of an aspiration needle coupled to an aspiration syringe according to another aspect of the present disclosure.
Figure 7:
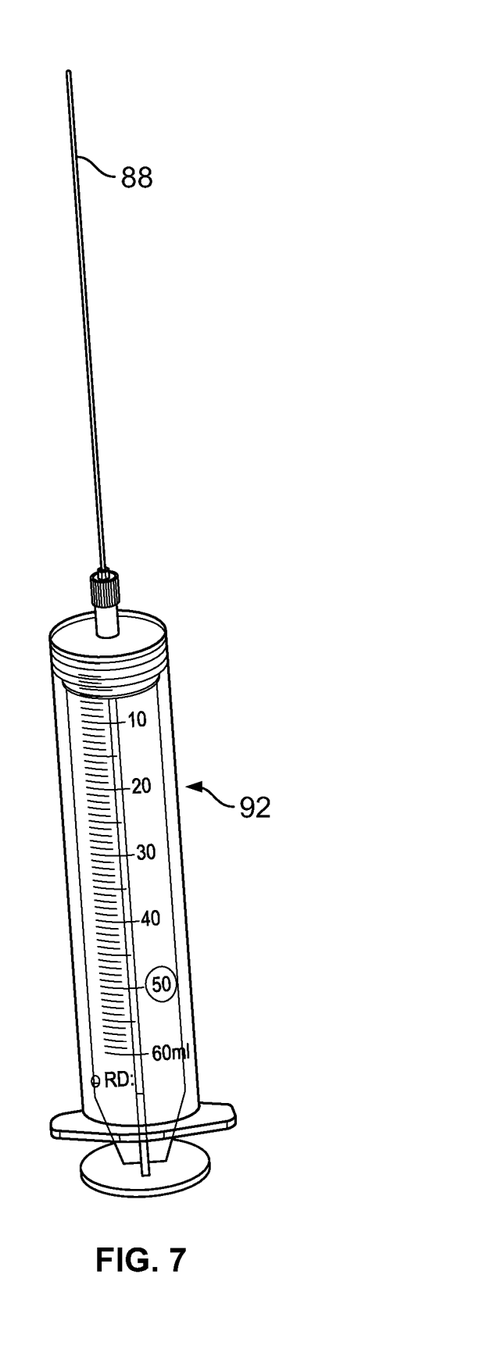
FIG. 7 is a perspective view of an injection needle coupled to an injection syringe according to another aspect of the present disclosure.

In yet another example, and referring now to FIGS. 6 and 7, there alternatively may be two separate syringes, such as the distal syringe 16 and the proximal syringe 22, that are not assembled together. In this example, an aspiration needle 67 (FIG. 6) may be directly coupled to the nozzle 60 of the distal syringe 16 and an injection needle 88 (FIG. 7) may be directly coupled to the nozzle 62 of the proximal syringe 22. In another example, each of the aspiration needle 67 and the injection needle 88 may alternatively be directly coupled to a body portion of a needle assembly, which is directly coupled to the nozzles 60, 62 or another portion of the distal and proximal syringes 16, 22, respectively. In yet another example, the aspiration needle 67 may be coupled to an aspiration syringe 90, as depicted in FIG. 6. The aspiration syringe 90 includes essentially all of the same components as the distal syringe 16, except the aspiration syringe 90 is not coupled to any other syringe. In addition, and as depicted in FIG. 7, the injection needle 88 may be coupled to an injection syringe 92, which is completely separate from, e.g., not assembled to, the aspiration syringe 90. In a similar manner, the injection syringe 92 includes essentially all of the same components as the proximal syringe 22, except the injection syringe 92 is not coupled to any other syringe.

So configured, the fluid from one of the proximal syringe 22 or the injection syringe 92 (FIG. 7) may be first injected into the target area TA (see, e.g., FIG. 4) using the injection needle 88. In this example, the proximal syringe 22 may be a stand-alone device that is not coupled to the distal syringe 16. After injection of the fluid in the target area TA is complete, tissue may then be extracted or aspirated from the same part of the target area TA using the needle 67 coupled to one of the distal syringe 16, which may be a stand-alone device separate from the proximal syringe 22 in this example, or the aspiration syringe 90 of FIG. 6. Said another way, fluid may be first inserted into the target area TA using the injection needle 88 before any tissue is extracted using the aspiration needle 67, as explained more below. Still further, one of ordinary skill in the art will understand that the injection and aspiration syringes 92, 90 may alternatively be referred as first and second syringes and still fall within the scope of the present disclosure. In this example, fluid may be added and then tissue extracted in sequence, such as incrementally, for one or more additional times. For example, 5 ml of saline fluid may be added and then 5 ml bone marrow may be extracted. Of course, one of ordinary skill in the art will appreciate that various other amount of fluid and tissue may be injected and extracted, respectively, and still fall within the scope of the present disclosure. In addition, in yet another example, the fluid added or injected may be more or less than the tissue extracted. Further, in some instances, creating positive pressure with the injection syringe 92 before extracting may be more advantageous than maintaining a pressure equilibrium, depending upon the tissue or bone being extracted, for example. In another example, the fluid may be injected and tissue then extracted in sequence for any one of two through twenty additional times. Of course, one of ordinary skill in the art will appreciate that the sequence may occur for more than twenty times, for example, and still fall within the scope of the present disclosure.

The device 10 described in the foregoing examples may be operated according to one of more of the following methods. For example, one method includes the device 10 extracting bone marrow from one of a first needle or the outer tube 68 of the needle 66 of the needle assembly 14 and into the chamber 20 of the distal syringe 16. In addition, the method further includes ejecting fluid from within the chamber 26 of the proximal syringe 22 through one of a second needle or the inner tube 70 of the needle 66 of the needle assembly 14 one of before or simultaneous to extracting the bone marrow, preventing negative pressure during aspiration.

In one example, extracting the bone marrow is extracting the bone marrow through the outer tube 68 of the needle 66 of the needle assembly 14, and ejecting fluid is ejecting fluid disposed within the chamber 26 of the proximal syringe 22 through the inner tube 70 of the needle 66 of the needle assembly 14. The method may further include controlling via the plunger 28, for example, a flow volume in each chamber 20, 26 of the distal syringe 16 and the proximal syringe 22, respectively. In this way, a volume of fluid ejected from the chamber 26 of the proximal syringe 22 is equal to a volume of bone marrow being extracted into the chamber 20 of the distal syringe 16. Further, the method may include actuating the plunger 28 toward the proximal syringe 22 to initiate aspiration.

In another example, the method may alternatively include ejecting fluid disposed within the chamber 26 of the proximal syringe 22 or the injection syringe 92 through a second needle different from a first needle. For example, the fluid may be injected from the injection syringe 92 through the injection needle 88 (FIG. 7) different from the aspiration needle 67 (FIG. 6), which is used to extract the bone marrow from the target area TA. In yet other examples, the method further comprises extracting the bone marrow through the extraction hole 80, such as a bore or other aperture, in the target area TA and injecting the fluid from the proximal syringe 22 or the injection syringe 92 into the same extraction hole 80. In yet another example, the method alternatively comprises extracting the bone marrow through the extraction hole 80 in the target area TA and injecting the fluid from one of the proximal syringe 22 or the injection syringe 92 into the injection hole 82 of the target area TA one or more of simultaneous to or before extracting the bone marrow.

In still another example, the device 10 and other devices and needles, for example, may implement the following method of aspirating bone marrow. The method includes extracting bone marrow from the aspiration hole 80 in the target area TA and injecting fluid through one or more of the aspiration hole 80 or the injection hole 82 in the target area TA one or more of simultaneous to or before extracting the bone marrow. In one example, extracting the bone marrow from the aspiration hole 80 includes extracting the bone marrow through one of an aspiration needle 67 coupled to the aspiration syringe 90 (FIG. 6) or the outer tube 68 of the needle 66 of the needle assembly 14. In addition, injecting fluid through one or more of the aspiration hole 80 or the separate injection hole 82 comprises injecting fluid through one of the injection needle 88 (FIG. 7) separate from the aspiration needle 67 or the inner tube 70 of the needle 66 of the needle assembly 14. In another example, extracting bone marrow from the aspiration hole 80 in the target area TA comprises extracting the bone marrow into one of the chamber 20 of the distal syringe 16 or the aspiration syringe 90. In addition, injecting fluid through one or more of the aspiration hole 80 or the separation injection hole 82 in the target area TA one or more of simultaneous to or before extracting the bone marrow comprises injecting fluid disposed within one of the chamber 26 of the proximal syringe 22 coupled to the distal syringe 16 or the injection syringe 92, a stand-alone device not coupled to any other syringe.

While the foregoing description refers to bone marrow being extracted from the target area TA, such as a bone in the target area TA, one of ordinary skill in the art will appreciate that any tissue from a subject may alternatively and/or additionally be extracted according to the device 10 and methods of the description and still fall within the scope of the present disclosure. More specifically, the device 10 and methods may be used to eliminate negative pressure during extraction of tissue, such as during a biopsy procedure, in any other part of the subject, such as a human body, including but not limited to bone in any other part of the subject outside of the spine, a breast area, or any other area of the subject.

One of ordinary skill in the art will appreciate the following advantages of the device 10 and methods described above. For example, the device 10 and methods mitigate patient pain caused by negative pressure in conventional bone marrow aspiration devices and methods by replacing fluid in the bone marrow space before or during aspiration of bone marrow. By replacing fluid in the marrow space, the rate of bone marrow withdrawal may be increased and the risk of damaging the bone marrow sample may be reduced. In addition, each of the foregoing methods ensures that negative pressure is not experienced by the patient during aspiration at least because the volume of fluid within the marrow space in each method is controlled. Said another way, the fluid volume is never less than it was at the beginning of the procedure during aspiration, ensuring negative pressure does not occur during aspiration. Thus, not only do the new device 10 and methods mitigate and/or completely eliminate patient pain, but also patient anxiety is reduced. As a result, there will be an increase in the number of patients opting to receive bone marrow and bone marrow stem cell treatments in an office, where they are safest and cheapest to perform.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Further, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A device for aspirating bone marrow, the device comprising:
a double syringe assembly including a distal syringe with a barrel having a chamber, a proximal syringe coupled to the distal syringe, the proximal syringe having a barrel with a chamber, and a single plunger having a distal end disposed within the barrel of the distal syringe and a proximal end disposed within the barrel of the proximal syringe; and
a needle assembly coupled to the double syringe assembly, the needle assembly having a needle with an outer tube and an inner tube disposed within the outer tube, a housing surrounding a portion of the needle, and a connector extending from the housing, the connector attached to the distal syringe,
wherein, upon actuation of the plunger in a direction toward the proximal syringe, the distal syringe extracts bone marrow from a target area through the outer tube of the needle and into the chamber of the distal syringe and the proximal syringe injects fluid into the target area through the inner tube of the needle at the same time and the same rate in which the bone marrow is extracted, the plunger controlling the flow volume of each syringe chamber such that the fluid volume ejected by the chamber of the proximal syringe is equal to the bone marrow volume received by the chamber of the distal syringe, and
where the inner tube of the needle is separate and sealed from the outer tube of the needle, preventing any bone marrow being extracted through the outer tube from mixing with any fluid being ejected from the proximal syringe into the inner tube.

2. The device of claim 1, further comprising a securing mechanism for coupling the distal syringe to the proximal syringe, such that the distal syringe is stationary relative to the proximal syringe.

3. The device of claim 1, wherein each of the distal syringe and the proximal syringe further comprises a base portion attached to each of the barrel of the distal syringe and the barrel of the proximal syringe, respectively, each base portion having at least one aperture or a plurality of apertures for receiving a securing mechanism to couple the distal syringe to the proximal syringe.

4. The device of claim 3, wherein the securing mechanism comprises at least one rod having a first end disposed within the at least one aperture of the base of the distal syringe and a second end disposed within the at least one aperture of the base of the proximal syringe, each end extending through the base and adapted to receive a fastener to secure the first and second ends of the rods to the bases of the distal and proximal syringes, respectively.

5. The device of claim 3, wherein the securing mechanism comprises a plurality of rods, each rod having a first end disposed within an aperture of the plurality of apertures of the base of the distal syringe, and a second end disposed within an aperture of the plurality of apertures of the base of the proximal syringe, each end extending through the aperture and adapted to receive a fastener to secure the ends of the rods to the bases of the distal and proximal syringes.

6. The device of claim 1, wherein the distal syringe further comprises a nozzle disposed on a distal end of the distal syringe, the nozzle coupled to the connector and the needle to form a fluid pathway between the outer tube of the needle and the chamber of the distal syringe.

7. The device of claim 1, wherein the proximal syringe further comprises a nozzle disposed on a proximal end of the proximal syringe, the nozzle coupled to the needle to form a fluid pathway between the inner tube of the needle and the chamber of the proximal syringe.

8. The device of claim 1, wherein the plunger is moveable from and between an unactuated state, in which the distal end of the plunger is adjacent to a nozzle of the distal syringe, and an extended state, in which the distal end of the plunger is adjacent to a base portion of the distal syringe.

9. The device of claim 1, wherein fluid disposed within the chamber of the proximal syringe before actuation of the plunger is one or more of a saline or other salt-balanced solution, an antibiotic, or an anesthetic.

10. A method of aspirating bone marrow comprising:
extracting bone marrow from a target area through one of an aspiration needle or an outer tube of a needle of a needle assembly and into a chamber of a distal syringe or an aspiration syringe; and
injecting fluid from a chamber of a proximal syringe or an injection syringe through one of an injection needle separate from the first needle or an inner tube of the needle of the needle assembly and into the target area one of before or simultaneous to extracting the bone marrow, the inner tube separate from and disposed within an outer tube of the aspiration needle through which the bone marrow is extracted, preventing negative pressure during aspiration.

11. The method of claim 10, wherein extracting bone marrow is extracting the bone marrow through the outer tube of the needle of the needle assembly, and injecting fluid is injecting fluid disposed within the chamber of the proximal syringe through the inner tube of the needle of the needle assembly, the method further comprising controlling a flow volume in each chamber of the distal syringe and the proximal syringe, such that a volume of fluid injected from the chamber of the proximal syringe is equal to a volume of bone marrow extracted by the distal syringe.

12. The method of claim 10, wherein extracting bone marrow comprises actuating a plunger having a first end disposed within a barrel of the distal syringe and a second end disposed within a barrel of the proximal syringe, such that the plunger moves toward the proximal end of the distal syringe to initiate aspiration.

13. The method of claim 10, wherein injecting fluid disposed within a chamber of the proximal syringe comprises injecting one or more of a saline or other salt-balanced sterile solution, an antibiotic, or an anesthetic disposed within the chamber of the proximal syringe through an inner tube of the aspiration needle before aspiration of the bone marrow.

14. The method of claim 10, wherein injecting fluid disposed within a chamber of the proximal syringe comprises injecting one or more of a saline or other salt-balanced sterile solution, an antibiotic, or an anesthetic disposed within the chamber of the proximal syringe through an inner tube of the aspiration needle simultaneous to aspiration of the bone marrow.

15. The method of claim 10, wherein injecting fluid disposed within a chamber of the proximal syringe comprises injecting one or more of a saline or other salt-balanced sterile solution, an antibiotic, or an anesthetic disposed within the chamber of the proximal syringe through a second needle one of before or simultaneous to aspiration of the bone marrow.

16. The method of claim 10, further comprising extracting the bone marrow through an aspiration hole in the target area and injecting fluid into the aspiration hole in the target area.

17. The method of claim 10, further comprising extracting the bone marrow through an aspiration hole and ejecting the fluid into an injection hole, the injection hole separate from the aspiration hole.

18. A method of aspirating bone marrow comprising:
extracting bone marrow from a target area through one of an aspiration needle or an outer tube of a needle of a needle assembly and into a chamber of a distal syringe or an aspiration syringe; and
injecting fluid from a chamber of a proximal syringe or an injection syringe through one of an injection needle separate from the first needle or an inner tube of the needle of the needle assembly and into the target area one of before or simultaneous to extracting the bone marrow, preventing negative pressure during aspiration,
wherein extracting bone marrow is extracting the bone marrow through the outer tube of the needle of the needle assembly, and injecting fluid is injecting fluid disposed within the chamber of the proximal syringe through the inner tube of the needle of the needle assembly, the method further comprising controlling a flow volume in each chamber of the distal syringe and the proximal syringe, such that a volume of fluid injected from the chamber of the proximal syringe is equal to a volume of bone marrow extracted by the distal syringe.

* * * * *